United States Patent [19]

Kamboj et al.

[11] Patent Number: 5,610,032
[45] Date of Patent: Mar. 11, 1997

[54] AMPA-BINDING HUMAN GLUR1 RECEPTORS

[75] Inventors: Rajender Kamboj, Mississauga; Candace E. Elliott; Stephen L. Nutt, both of Etobicoke, all of Canada

[73] Assignee: Allelix Biopharmaceutical Inc., Mississauga, Canada

[21] Appl. No.: 254,573

[22] Filed: Jun. 6, 1994

Related U.S. Application Data

[63] Continuation of Ser. No. 896,611, Jun. 10, 1992, abandoned.

[51] Int. Cl.$^6$ .................................................. C12N 15/00
[52] U.S. Cl. .................. 435/69.1; 435/70.1; 435/172.3; 435/252.3; 536/23.1; 536/23.5; 536/25.3
[58] Field of Search .................................. 536/23.1, 23.5, 536/25.3; 435/6, 69.1, 70.1, 70.3, 172.3, 240.2, 252.3, 320.1, 270, 810; 436/63; 514/44; 935/1, 9, 10, 19, 52, 53, 70

[56] References Cited

PUBLICATIONS

Potier et al. "The human glutamate receptor cDNA GluR1: cloning sequencing, expression and localization . . . ", *DNA Seq.–J. DNA Seq. and Mapping*, 2:211–218 (1992).
Sun et al, Proc. Natl. Acad. Sci. USA, vol. 89, pp. 1443–1447, Feb. 1992.
Puckett et al, Proc. Natl. Acad. Sci. USA, vol. 88, pp. 7557–7561, Sep. 1991.
Hollmann et al, Nature 1989 342:643.
Keinanen et al, Science 1990 249:556.
Boulter et al, Science 1990 249:1033.
Bettler et al, Neuron 1990 5:583.
Sommer et al, Science 1990 249:1580.
Monyer et al, Neuron 1991 6:799.
Nakanishi et al, Neuron 1990 5:569.
Hollmann et al, Science 1991 252:851.
Verdoorn et al, Science 1991 252:1715.
Egebjerg et al, Nature 1991 351:745.
Wada et al, Nature 1991 342:684.
Gregor et al, Nature 1989 342:689.
Werner et al, Nature 1991 351:742.
Barnett et al, Nucleic Acids Res. 1990 18(10):3094.

*Primary Examiner*—Christine M. Nucker
*Assistant Examiner*—Laurie Scheiner
*Attorney, Agent, or Firm*—Foley & Lardner

[57] ABSTRACT

Described herein are isolated polynucleotides which code for an AMPA-type human CNS receptor, designated the human GluR1B receptor. The receptor is characterized structurally and the construction and use of cell lines expressing the receptor is disclosed.

14 Claims, 8 Drawing Sheets

FIG. IA

```
        EcoRI
          |
        GAATTCCACACCAAATCTATGATTGGACCTGGGCTTCTTTTTCGCCAATGCAAAAGGAA
   1    ----------+---------+---------+---------+---------+---------+   60
        CTTAAGGTGTGGTTTAGATACTAACCTGGACCCGAAGAAAAAGCGGTTACGTTTTTCCTT

TATGCAGCACATTTTTGCCTTCTTCTGCACCGGTTTCCTAGGCGCGGTAGTAGGTGCCAA
  61    ----------+---------+---------+---------+---------+---------+  120
        ATACGTCGTGTAAAAACGGAAGAAGACGTGGCCAAAGGATCCGCGCCATCATCCACGGTT

M  Q  H  I  F  A  F  F  C  T  G  F  L  G  A  V  V  G  A  N  -
                                                               └─MATURE

TTTCCCCAACAATATCCAGATCGGGGGATTATTTCCAAACCAGCAGTCACAGGAACATGC
 121    ----------+---------+---------+---------+---------+---------+  180
        AAAGGGGTTGTTATAGGTCTAGCCCCCTAATAAAGGTTTGGTCGTCAGTGTCCTTGTACG

F  P  N  N  I  Q  I  G  G  L  F  P  N  Q  Q  S  Q  E  H  A  -

TGCTTTTAGATTTGCTTTGTCGCAACTCACAGAGCCCCCGAAGCTGCTCCCCCAGATTGA
 181    ----------+---------+---------+---------+---------+---------+  240
        ACGAAAATCTAAACGAAACAGCGTTGAGTGTCTCGGGGGCTTCGACGAGGGGGTCTAACT

A  F  R  F  A  L  S  Q  L  T  E  P  P  K  L  L  P  Q  I  D  -

TATTGTGAACATCAGCGACACGTTTGAGATGACCTATAGATTCTGTTCCCAGTTCTCCAA
 241    ----------+---------+---------+---------+---------+---------+  300
        ATAACACTTGTAGTCGCTGTGCAAACTCTACTGGATATCTAAGACAAGGGTCAAGAGGTT

I  V  N  I  S  D  T  F  E  M  T  Y  R  F  C  S  Q  F  S  K  -

AGGAGTCTATGCCATCTTTGGGTTTTATGAACGTAGGACTGTCAACATGCTGACCTCCTT
 301    ----------+---------+---------+---------+---------+---------+  360
        TCCTCAGATACGGTAGAAACCCAAAATACTTGCATCCTGACAGTTGTACGACTGGAGGAA

G  V  Y  A  I  F  G  F  Y  E  R  R  T  V  N  M  L  T  S  F  -

TTGTGGGGCCCTCCACGTCTGCTTCATTACGCCGAGCTTTCCCGTTGATACATCCAATCA
 361    ----------+---------+---------+---------+---------+---------+  420
        AACACCCCGGGAGGTGCAGACGAAGTAATGCGGCTCGAAAGGGCAACTATGTAGGTTAGT

C  G  A  L  H  V  C  F  I  T  P  S  F  P  V  D  T  S  N  Q  -

GTTTGTCCTTCAGCTGCGCCCTGAACTGCAGGATGCCCTCATCAGCATCATTGACCATTA
 421    ----------+---------+---------+---------+---------+---------+  480
        CAAACAGGAAGTCGACGCGGGACTTGACGTCCTACGGGAGTAGTCGTAGTAACTGGTAAT

F  V  L  Q  L  R  P  E  L  Q  D  A  L  I  S  I  I  D  H  Y  -

CAAGTGGCAGAAATTTGTCTACATTTATGATGCCGACCGGGGCTTATCCGTCCTGCAGAA
 481    ----------+---------+---------+---------+---------+---------+  540
        GTTCACCGTCTTTAAACAGATGTAAATACTACGGCTGGCCCCGAATAGGCAGGACGTCTT

K  W  Q  K  F  V  Y  I  Y  D  A  D  R  G  L  S  V  L  Q  K  -

AGTCCTGGATACAGCTGCTGAGAAGAACTGGCAGGTGACAGCAGTCAACATTTTGACAAC
 541    ----------+---------+---------+---------+---------+---------+  600
        TCAGGACCTATGTCGACGACTCTTCTTGACCGTCCACTGTCGTCAGTTGTAAAACTGTTG

```
     CACAGAGGAGGGATACCGGATGCTCTTTCAGGACCTGGAGAAGAAAAAGGAGCGGCTGGT
601  ------------------------------------------------------------  660
     GTGTCTCCTCCCTATGGCCTACGAGAAAGTCCTGGACCTCTTCTTTTTCCTCGCCGACCA

T  E  E  G  Y  R  M  L  F  Q  D  L  E  K  K  K  E  R  L  V  -

GGTGGTGGACTGTGAATCAGAACGCCTCAATGCTATCTTGGGCCAGATTATAAAGCTAGA
661  ------------------------------------------------------------  720
     CCACCACCTGACACTTAGTCTTGCGGAGTTACGATAGAACCCGGTCTAATATTTCGATCT

V  V  D  C  E  S  E  R  L  N  A  I  L  G  Q  I  I  K  L  E  -

GAAGAATGGCATCGGCTACCACTACATTCTTGCAAATCTGGGCTTCATGGACATTGACTT
721  ------------------------------------------------------------  780
     CTTCTTACCGTAGCCGATGGTGATGTAAGAACGTTTAGACCCGAAGTACCTGTAACTGAA

K  N  G  I  G  Y  H  Y  I  L  A  N  L  G  F  M  D  I  D  L  -

AAACAAATTCAAGGAGAGTGGCGCCAATGTGACAGGTTTCCAGCTGGTGAACTACACAGA
781  ------------------------------------------------------------  840
     TTTGTTTAAGTTCCTCTCACCGCGGTTACACTGTCCAAAGGTCGACCACTTGATGTGTCT

N  K  F  K  E  S  G  A  N  V  T  G  F  Q  L  V  N  Y  T  D  -

CACTATTCCGGCCAAGATCATGCAGCAGTGGAAGAATAGTGATGCTCGAGACCACACACG
841  ------------------------------------------------------------  900
     GTGATAAGGCCGGTTCTAGTACGTCGTCACCTTCTTATCACTACGAGCTCTGGTGTGTGC

T  I  P  A  K  I  M  Q  Q  W  K  N  S  D  A  R  D  H  T  R  -

GGTGGACTGGAAGAGACCCAAGTACACCTCTGCGCTCACCTACGATGGGGTGAAGGTGAT
901  ------------------------------------------------------------  960
     CCACCTGACCTTCTCTGGGTTCATGTGGAGACGCGAGTGGATGCTACCCCACTTCCACTA

V  D  W  K  R  P  K  Y  T  S  A  L  T  Y  D  G  V  K  V  M  -

GGCTGAGGCTTTCCAGAGCCTGCGGAGGCAGAGAATTGATATATCTCGCCGGGGGAATGC
961  ------------------------------------------------------------ 1020
     CCGACTCCGAAAGGTCTCGGACGCCTCCGTCTCTTAACTATATAGAGCGGCCCCCTTACG

A  E  A  F  Q  S  L  R  R  Q  R  I  D  I  S  R  R  G  N  A  -

TGGGGATTGTCTGGCTAACCCAGCTGTTCCCTGGGGCCAAGGGATCGACATCCAGAGAGC
1021 ------------------------------------------------------------ 1080
     ACCCCTAACAGACCGATTGGGTCGACAAGGGACCCCGGTTCCCTAGCTGTAGGTCTCTCG

G  D  C  L  A  N  P  A  V  P  W  G  Q  G  I  D  I  Q  R  A  -

TCTGCAGCAGGTGCGATTTGAAGGTTTAACAGGAAACGTGCAGTTTAATGAGAAAGGACG
1081 ------------------------------------------------------------ 1140
     AGACGTCGTCCACGCTAAACTTCCAAATTGTCCTTTGCACGTCAAATTACTCTTTCCTGC

L  Q  Q  V  R  F  E  G  L  T  G  N  V  Q  F  N  E  K  G  R  -

CCGGACCAACTACACGCTCCACGTGATTGAAATGAAACATGACGGCATCCGAAAGATTGG
1141 ------------------------------------------------------------ 1200
     GGCCTGGTTGATGTGCGAGGTGCACTAACTTTACTTTGTACTGCCGTAGGCTTTCTAACC

```
     TTACTGGAATGAAGATGATAAGTTTGTCCCTGCAGCCACCGATGCCCAAGCTGGGGCGA
1201 ---------+---------+---------+---------+---------+---------+ 1260
     AATGACCTTACTTCTACTATTCAAACAGGGACGTCGGTGGCTACGGGTTCGACCCCCGCT

Y  W  N  E  D  D  K  F  V  P  A  A  T  D  A  Q  A  G  G  D  -

TAATTCAAGTGTTCAGAACAGAACATACATCGTCACAACAATCCTAGAAGATCCTTATGT
1261 ---------+---------+---------+---------+---------+---------+ 1320
     ATTAAGTTCACAAGTCTTGTCTTGTATGTAGCAGTGTTGTTAGGATCTTCTAGGAATACA

N  S  S  V  Q  N  R  T  Y  I  V  T  T  I  L  E  D  P  Y  V  -

GATGCTCAAGAAGAACGCCAATCAGTTTGAGGGCAATGACCGTTACGAGGGCTACTGTGT
1321 ---------+---------+---------+---------+---------+---------+ 1380
     CTACGAGTTCTTCTTGCGGTTAGTCAAACTCCCGTTACTGGCAATGCTCCCGATGACACA

M  L  K  K  N  A  N  Q  F  E  G  N  D  R  Y  E  G  Y  C  V  -

AGAGCTGGCGGCAGAGATTGCCAAGCACGTGGGCTACTCCTACCGTCTGGAGATTGTCAG
1381 ---------+---------+---------+---------+---------+---------+ 1440
     TCTCGACCGCCGTCTCTAACGGTTCGTGCACCCGATGAGGATGGCAGACCTCTAACAGTC

E  L  A  A  E  I  A  K  H  V  G  Y  S  Y  R  L  E  I  V  S  -

TGATGGAAAATACGGAGCCCGAGACCCTGACACGAAGGCCTGGAATGGCATGGTGGGAGA
1441 ---------+---------+---------+---------+---------+---------+ 1500
     ACTACCTTTTATGCCTCGGGCTCTGGGACTGTGCTTCCGGACCTTACCGTACCACCCTCT

D  G  K  Y  G  A  R  D  P  D  T  K  A  W  N  G  M  V  G  E  -

GCTGGTCTATGGAAGAGCAGATGTGGCTGTGGCTCCCTTAACTATCACTTTGGTCCGGGA
1501 ---------+---------+---------+---------+---------+---------+ 1560
     CGACCAGATACCTTCTCGTCTACACCGACACCGAGGGAATTGATAGTGAAACCAGGCCCT

L  V  Y  G  R  A  D  V  A  V  A  P  L  T  I  T  L  V  R  E  -

AGAAGTTATAGATTTCTCCAAACCATTTATGAGTTTGGGGATCTCCATCATGATTAAAAA
1561 ---------+---------+---------+---------+---------+---------+ 1620
     TCTTCAATATCTAAAGAGGTTTGGTAAATACTCAAACCCCTAGAGGTAGTACTAATTTTT

E  V  I  D  F  S  K  P  F  M  S  L  G  I  S  I  M  I  K  K  -

ACCACAGAAATCCAAGCCGGGTGTCTTCTCCTTCCTTGATCCTTTGGCTTATGAGATTTG
1621 ---------+---------+---------+---------+---------+---------+ 1680
     TGGTGTCTTTAGGTTCGGCCCACAGAAGAGGAAGGAACTAGGAAACCGAATACTCTAAAC

P  Q  K  S  K  P  G  V  F  S  F  L  D  P  L  A  Y  E  I  W  -

GATGTGCATTGTTTTTGCCTACATTGGAGTGAGTGTTGTCCTCTTCCTGGTCAGCCGCTT
1681 ---------+---------+---------+---------+---------+---------+ 1740
     CTACACGTAACAAAAACGGATGTAACCTCACTCACAACAGGAGAAGGACCAGTCGGCGAA

M  C  I  V  F  A  Y  I  G  V  S  V  V  L  F  L  V  S  R  F  -

CAGTCCCTATGAATGGCACAGTGAAGAGTTTGAGGAAGGACGGGACCAGACAACCAGTGA
1741 ---------+---------+---------+---------+---------+---------+ 1800
     GTCAGGGATACTTACCGTGTCACTTCTCAAACTCCTTCCTGCCCTGGTCTGTTGGTCACT

```
      CCAGTCCAATGAGTTTGGGATATTCAACAGTTTGTGGTTCTCCCTGGGAGCCTTCATGCA
1801  ------------------------------------------------------------  1860
      GGTCAGGTTACTCAAACCCTATAAGTTGTCAAACACCAAGAGGGACCCTCGGAAGTACGT

Q  S  N  E  F  G  I  F  N  S  L  W  F  S  L  G  A  F  M  Q  -

GCAAGGATGTGACATTTCTCCCAGGTCCCTGTCTGGTCGCATCGTTGGTGGCGTCTGGTG
1861  ------------------------------------------------------------  1920
      CGTTCCTACACTGTAAAGAGGGTCCAGGGACAGACCAGCGTAGCAACCACCGCAGACCAC

Q  G  C  D  I  S  P  R  S  L  S  G  R  I  V  G  G  V  W  W  -

GTTCTTCACCTTAATCATCATCTCCTCATATACAGCCAATCTGGCCGCCTTCCTGACCGT
1921  ------------------------------------------------------------  1980
      CAAGAAGTGGAATTAGTAGTAGAGGAGTATATGTCGGTTAGACCGGCGGAAGGACTGGCA

F  F  T  L  I  I  I  S  S  Y  T  A  N  L  A  A  F  L  T  V  -

GGAGAGGATGGTGTCTCCCATTGAGAGTGCAGAGGACCTAGCGAACGAGACAGAAATTGC
1981  ------------------------------------------------------------  2040
      CCTCTCCTACCACAGAGGGTAACTCTCACGTCTCCTGGATCGCTTGCTCTGTCTTTAACG

E  R  M  V  S  P  I  E  S  A  E  D  L  A  N  E  T  E  I  A  -

CTACGGGACGCTGGAAGCAGGATCTACTAAGGAGTTCTTCAGGAGGTCTAAAATTGCTGT
2041  ------------------------------------------------------------  2100
      GATGCCCTGCGACCTTCGTCCTAGATGATTCCTCAAGAAGTCCTCCAGATTTTAACGACA

Y  G  T  L  E  A  G  S  T  K  E  F  F  R  R  S  K  I  A  V  -

GTTTGAGAAGATGTGGACATACATGAAGTCAGCAGAGCCATCAGTTTTTGTGCGGACCAC
2101  ------------------------------------------------------------  2160
      CAAACTCTTCTACACCTGTATGTACTTCAGTCGTCTCGGTAGTCAAAAACACGCCTGGTG

F  E  K  M  W  T  Y  M  K  S  A  E  P  S  V  F  V  R  T  T  -

AGAGGAGGGGATGATTCGAGTGAGGAAATCCAAAGGCAAATATGCCTACCTCCTGGAGTC
2161  ------------------------------------------------------------  2220
      TCTCCTCCCCTACTAAGCTCACTCCTTTAGGTTTCCGTTTATACGGATGGAGGACCTCAG

E  E  G  M  I  R  V  R  K  S  K  G  K  Y  A  Y  L  L  E  S  -

CACCATGAATGAGTACATTGAGCAGCGGAAACCCTGTGACACCATGAAGGTGGGAGGTAA
2221  ------------------------------------------------------------  2280
      GTGGTACTTACTCATGTAACTCGTCGCCTTTGGGACACTGTGGTACTTCCACCCTCCATT

T  M  N  E  Y  I  E  Q  R  K  P  C  D  T  M  K  V  G  G  N  -

CTTGGATTCCAAAGGCTATGGCATTGCAACACCCAAGGGGTCTGCCCTGAGAGGTCCCGT
2281  ------------------------------------------------------------  2340
      GAACCTAAGGTTTCCGATACCGTAACGTTGTGGGTTCCCCAGACGGGACTCTCCAGGGCA

L  D  S  K  G  Y  G  I  A  T  P  K  G  S  A  L  R  G  P  V  -

AAACCTAGCGGTTTTGAAACTCAGTGAGCAAGGCGTCTTAGACAAGCTGAAAAGCAAATG
2341  ------------------------------------------------------------  2400
      TTTGGATCGCCAAAACTTTGAGTCACTCGTTCCGCAGAATCTGTTCGACTTTTCGTTTAC

```
     GTGGTACGATAAAGGGGAATGTGGAAGCAAGGACTCCGGAAGTAAGGACAAGACAAGCGC
2401 ---------+---------+---------+---------+---------+---------+ 2460
     CACCATGCTATTTCCCCTTACACCTTCGTTCCTGAGGCCTTCATTCCTGTTCTGTTCGCG

W   Y   D   K   G   E   C   G   S   K   D   S   G   S   K   D   K   T   S   A   -

TCTGAGCCTCAGCAATGTGGCAGGCGTGTTCTACATCCTGATCGGAGGACTTGGACTAGC
2461 ---------+---------+---------+---------+---------+---------+ 2520
     AGACTCGGAGTCGTTACACCGTCCGCACAAGATGTAGGACTAGCCTCCTGAACCTGATCG

L   S   L   S   N   V   A   G   V   F   Y   I   L   I   G   G   L   G   L   A   -

CATGCTGGTTGCCTTAATCGAGTTCTGCTACAAATCCCGTAGTGAATCCAAGCGGATGAA
2521 ---------+---------+---------+---------+---------+---------+ 2580
     GTACGACCAACGGAATTAGCTCAAGACGATGTTTAGGGCATCACTTAGGTTCGCCTACTT

M   L   V   A   L   I   E   F   C   Y   K   S   R   S   E   S   K   R   M   K   -

GGGTTTTTGTTTGATCCCACAGCAATCCATCAACGAAGCCATACGGACATCGACCCTCCC
2581 ---------+---------+---------+---------+---------+---------+ 2640
     CCCAAAAACAAACTAGGGTGTCGTTAGGTAGTTGCTTCGGTATGCCTGTAGCTGGGAGGG

G   F   C   L   I   P   Q   Q   S   I   N   E   A   I   R   T   S   L   P   -

CCGCAACAGCGGGGCAGGAGCCAGCAGCGGCGGCAGTGGAGAGAATGGTCGGGTGGTCAG
2641 ---------+---------+---------+---------+---------+---------+ 2700
     GGCGTTGTCGCCCCGTCCTCGGTCGTCGCCGCCGTCACCTCTCTTACCAGCCCACCAGTC

R   N   S   G   A   G   A   S   S   G   G   S   G   E   N   G   R   V   V   S   -

CCATGACTTCCCCAAGTCCATGCAATCGATTCCTTGCATGAGCCACAGTTCAGGGATGCC
2701 ---------+---------+---------+---------+---------+---------+ 2760
     GGTACTGAAGGGGTTCAGGTACGTTAGCTAAGGAACGTACTCGGTGTCAAGTCCCTACGG

H   D   F   P   K   S   M   Q   S   I   P   C   M   S   H   S   S   G   M   P   -

CTTGGGAGCCACGGGATTGTAACTGGAGCAGATGGAGACCCCTTGGGGAGCAGGCTCGGG
2761 ---------+---------+---------+---------+---------+---------+ 2820
     GAACCCTCGGTGCCCTAACATTGACCTCGTCTACCTCTGGGGAACCCCTCGTCCGAGCCC

L   G   A   T   G   L   *

CTCCCCAGCCCCATCCCAAACCCTTCAGTGCCAAAAACAACAACAAAATAGAAAGCGCAA
2821 ---------+---------+---------+---------+---------+---------+ 2880
     GAGGGGTCGGGGTAGGGTTTGGGAAGTCACGGTTTTGTTGTTGTTTTATCTTTCGCGTT

CCACCACCAACCACTGCGACCACAAGAAGGATGATTCAACAGGTTTTCCTGAAGAATTGA
2881 ---------+---------+---------+---------+---------+---------+ 2940
     GGTGGTGGTTGGTGACGCTGGTGTTCTTCCTACTAAGTTGTCCAAAAGGACTTCTTAACT

AAAACCATTTTGCTGTCCCTTTTCCTTTTTTGATGTTCTTTCACCCTTTTCTGTTTGCTA
2941 ---------+---------+---------+---------+---------+---------+ 3000
     TTTTGGTAAAACGACAGGGAAAAGGAAAAAACTACAAGAAAGTGGGAAAAGACAAACGAT

AGTGAGGATGAAAAAATAACACTGTACTGCAATAAGGGGAGAGTAACCCTGTCTAATGAA
3001 ---------+---------+---------+---------+---------+---------+ 3060
     TCACTCCTACTTTTTTATTGTGACATGACGTTATTCCCCTCTCATTGGGACAGATTACTT
```

FIG. 1F

```
      ACCTGTGTCTCTGAGAGTAGAGTCACTGGAACACTAATGAGGAAACTGCACTGTTTTATT
3061  ------+---------+---------+---------+---------+---------+  3120
      TGGACACAGAGACTCTCATCTCAGTGACCTTGTGATTACTCCTTGACGTGACAAAATAA

TTAATTCAGTTGTTAGTGTGTCTTAGTGTGTGCAATTTTTTTCTTACTAATATCCATGG
3121  ------+---------+---------+---------+---------+---------+  3180
      AATTAAGTCAACAATCACACAGAATCACACACGTTAAAAAAAGAATGATTATAGGTACC

EcoRI
                                          --
      TTTGCAGGTTCTGTGTTAGGCCCTTTCCTTCCTCCCTGGAATTC
3181  ------+---------+---------+---------+-----+  3220
      AAACGTCCAAGACAATCCGGGAAAGGAAGAGGACCTTAAG
```

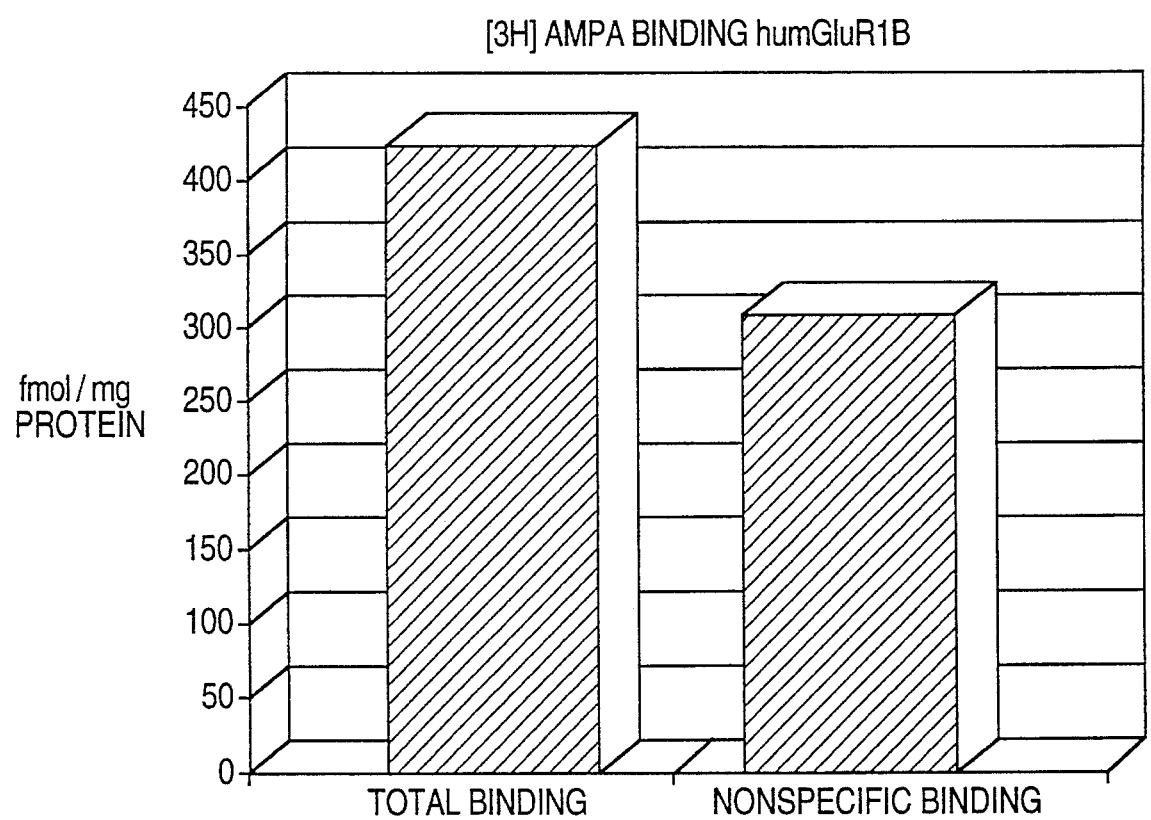

AMPA-BINDING HUMAN GLUR1 RECEPTORS

This application is a continuation, of application Ser. No. 07/896,611, filed Jun. 10, 1992, now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND OF THE INVENTION

In the mammalian central nervous system (CNS), the transmission of nerve impluses is controlled by the interaction between a neurotransmitter substance released by the "sending" neuron which binds to a surface receptor on the "receiving" neuron, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Very recently, genes encoding substituent polypeptides of EAA receptors from non-human sources, principally rat, have been discovered. Hollmann et al., Nature 342: 643, 1989 described the isolation from rat of a gene referred to originaily as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettier et al., Neuron 5: 583. 1990 described GluR5. Keinanen et al., supra, described genes called GluR-A, GluR-B, GluR-C and GluR-D which correspond precisely to GluR1, GluR2, GluR3 and GluR4 respectively. Sommer et al., Science 249: 1580, 1990 also showed, for GluR-A, GluR-B, GluR-C and GluR-D two alternatively spliced forms for each gene. These authors, as well as Monyer et al., Neuron 6: 799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et al., Science 252: 851, 1991; Verdoorn et al., Science 252: 1715, 1991; and see WO 91/06648).

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

SUMMARY OF THE INVENTION

The present invention provides an isolated polynucleotide that codes for an AMPA-binding human EAA receptor. By providing polynucleotide that codes specifically for a CNS receptor native to humans, the present invention provides means for evaluating the human nervous system, and particularly for assessing potentially therapeutic interactions between the AMPA-binding human EAA receptors and selected natural and synthetic ligands.

In one of its aspects, the present invention provides an isolated polynucleotide comprising nucleic acids arranged in a sequence that codes for a human EAA receptor herein designated the human GluR1B receptor. Alternatively, the polynucleotide may code for an AMPA-binding fragment of the human GluR1B receptor, or for an AMPA-binding variant of the human GluR1B receptor. In various specific embodiments of the present invention, the polynucleotide consists of DNA e.g. cDNA, or of RNA e.g. messenger RNA. In other embodiments of the present invention, the polynucleotide may be coupled to a reporter molecule, such as a radioactive label, for use in autoradiographic studies of human GluR1B receptor tissue distribution. In further embodiments of the present invention, fragments of the polynucleotides of the invention, including radiolabelled versions thereof, may be employed either as probes for detection of glutamate receptor-encoding polynucleotides, as primers appropriate for amplifying such polynucleotides present in a biological specimen, or as templates for expression of the human GluR1B receptor or an AMPA-binding fragment of variant thereof.

According to another aspect of the present invention, there is provided a cellular host having incorporated therein a polynucleotide of the present invention. In embodiments of the present invention, the polynucleotide is a DNA molecule and is incorporated for expression and secretion in the cellular host, to yield a functional, membrane-bound human GluR1B receptor or to yield an AMPA-binding fragment or variant of the human GluR1B receptor. In other embodiments of the present invention, the polynucleotide is an RNA molecule which is incorporated in the cellular host to yield the human GluR1B receptor as a functional, membrane-bound product of translation.

According to another aspect of the invention, there is provided a process for obtaining a substantially homogeneous source of a human EAA receptor useful for performing ligand binding assays, which comprises the steps of culturing a genetically engineered cellular host of the invention, and then recovering the cultured cells. Optionally, the cultured cells may be treated to obtain membrane preparations thereof, for use in the ligand binding assays.

According to another aspect of the present invention, there is provided a method for assessing the binding interaction between a test compound and a human CNS receptor, which comprises the steps of incubating the test compound under appropriate conditions with a human GluR1B receptor source, i.e., a cellular host of the invention or a membrane preparation derived therefrom, and then determining the extent or result of binding between the substance and the receptor source.

These and other aspects of the invention are now described in greater detail with reference to the accompanying drawings, in which:

BRIEF REFERENCE TO THE DRAWINGS

FIG. 1 provides a DNA sequence (SEQ ID NO:1) coding for the human GluR1B receptor, and the amino acid sequence (SEQ ID NO:1) thereof;

FIG. 2 depicts the strategy employed in generating recombinant DNA expression constructs incorporating the human GluR1B receptor-encoding DNA of FIG. 1 (the sequence shown in FIG. 3 are also disclosed in SEQ ID NOs. 3 and 4); and FIG. 3 illustrates the AMPA-binding property of the human GluR1B receptor.

DETAILED DESCRIPTION OF THE INVENTION AND ITS PREFERRED EMBODIMENTS

Figure 2:
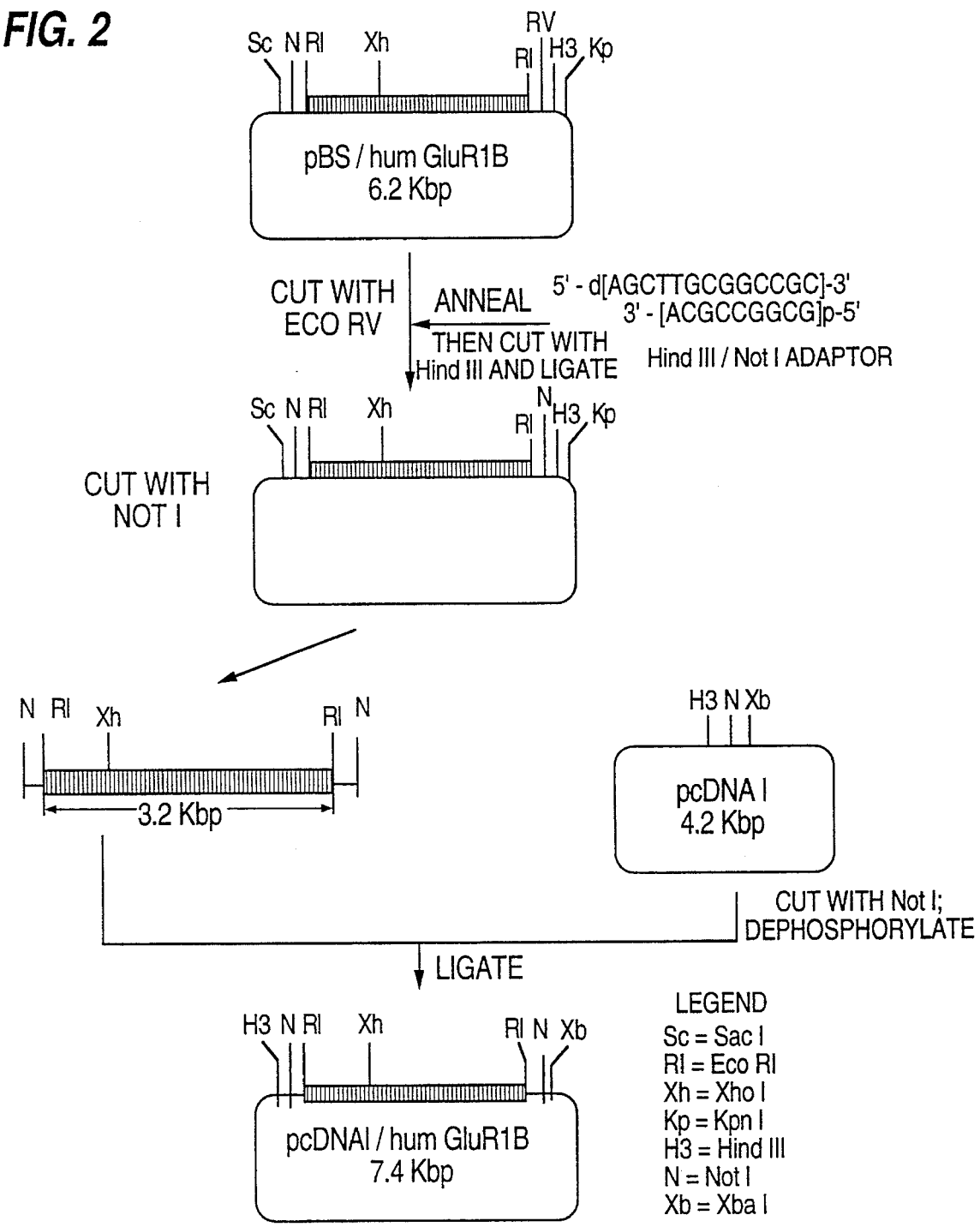

The invention relates to human CNS receptors of the AMPA-binding type, and provides isolated polynucleotides that code for such receptors. The term "isolated" is used herein with reference to intact polynucleotides that are generally less than about 4,000 nucleotides in length and which are otherwise isolated from DNA coding for other human proteins.

In the present context, human CNS receptors of the AMPA-binding type exhibit a characteristic ligand binding profile, which reveals glutamate binding and relative greater affinity for binding AMPA than for other binding other CNS receptor ligands such as kainate, glutamate and their closely related analogues.

In the present specification, an AMPA-binding receptor is said to be "functional" if a cellular host producing it exhibits de novo channel activity when exposed appropriately to AMPA, as determined by the established electrophysiological assays described for example by Hollman et al, supra, or by any other assay appropriate for detecting conductance across a cell membrane.

The human GluR1B receptor of the invention possess structural features characteristic of the EAA receptors in general, including extracellular N- and C-terminal regions, as well as four internal hydrophobic domains which serve to anchor the receptor within the cell surface membrane. More specifically, GluR1B receptor is a protein characterized structurally as a single polypeptide chain that is produced initially in precursor form bearing an 18 amino acid residue N-terminal signal peptide, and is transported to the cell surface in mature form, lacking the signal peptide and consisting of 888 amino acids arranged in the sequence illustrated, by single letter code, in FIG. 1 and SEQ ID NOs. 1 and 2. Unless otherwise stated, the term human GluR1B receptor refers to the mature form of the receptor, and amino acid residues of the human GluR1B receptor are accrodingly numbered with reference to the mature protein sequence. With respect to structural domains of the receptor, hydropathy analysis reveals four putative transmembrane domains, one spanning residues 521–540 inclusive (TM-1), another spanning residues 567–585 (TM-2), a third spanning residues 596–614 (TM-3) and the fourth spanning residues 788–808 (TM-4). Based on this assignment, it is likely that the human GluR1B receptor structure, in its natural membrane-bound form, consists of a 520 amino acid N-terminal extracellular domain, followed by a hydrophobic region containing four transmembrane domains and an extracellular, 80 amino acid C-terminal domain.

Binding assays performed with various ligands, and with membrane preparations derived from mammalian cells engineered genetically to produce the human GluR1B receptor in membrane-bound form indicate that GluR1B binds selectively to AMPA, relative particularly to kainate and NMDA. This feature, coupled with the medically significant connection between AMPA-type receptors and neurological disorders and disease indicate that the present receptor, and its AMPA-binding fragments and variants, will serve as valuable tools in the screening and discovery of ligands useful to modulate in vivo interactions between such receptors and their natural ligand, glutamate. Thus, a key aspect of the present invention resides in the construction of cells that are engineered genetically to produce human GluR1B receptor, to serve as a ready and homogeneous source of receptor for use in in vitro ligand binding and/or channel activation assays.

For use in the ligand binding assays, it is desirable to construct by application of genetic engineering techniques a mammalian cell that produces a human GluR1B receptor as a heterologous, membrane-bound product. According to one embodiment of the invention, the construction of such engineered cells is achieved by introducing into a selected host cell a recombinant DNA secretion construct in which DNA coding for a secretable form of the human GluR1B receptor i.e., a form of the receptor bearing its native signal peptide or a functional, heterologous equivalent thereof, is linked operably with expression controlling elements that are functional in the selected host to drive expression of the receptor-encoding DNA, and thus elaborate the receptor protein in its desired, mature and membrane-bound form. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human GluR1B receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevetheless serve as expression hosts, provided that "background" binding to the test ligand is accounted for in the assay results.

According to one embodiment of the present invention, the cell line selected to serve as host for human GluR1B receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for the receptor in secretable form is linked with expression controlling DNA sequences recognized by the host, and which include a region 5' of the receptor-encoding DNA to drive expression, and a 3' region to terminate expression. The plasmidic vector harbouring the recombinant DNA expression construct typically incorporates such other functional components as an origin of replication, usually virally-derived, to permit replication of the plasmid in the expression host and desirably also for plasmid amplification in a bacterial host, such as E. coli. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e. the metalothionein gene promoter, and other steroid-inducible promoters.

For incorporation into the recombinant DNA expression vector, DNA coding for the human GluR1B receptor, or an AMPA-binding fragment or variant thereof, can be obtained by applying selected techniques of gene isolation or gene synthesis. As described in more detail in the examples herein, the human GluR1B receptor is encoded within the genome of human brain tissue, and can therefore be obtained from human DNA libraries by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in for example a bacterial plasmid, more typically a bacteriophage. Such bacteriophage harbouring fragments of the human DNA are typically grown by plating on a lawn of susceptible E. coli bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof, Typically, the gene or a portion thereof so identified is subcloned into a plasmidic vector for nucleic acid sequence analysis.

In a specific embodiment of the invention, the GluR1B receptor is encoded by the DNA sequence illustrated in FIG. 1 and SEQ ID NO:1. In an obvious alternative, the DNA sequences coding for the selected receptor may be a synonymous codon equivalent of the illustrated DNA sequences.

The illustrated DNA sequence constitutes the cDNA sequence identified in human brain cDNA libraries in the manner exemplified herein. Having herein provided the nucleotide sequence of the human GluR1B receptor, however, it will be appreciated that polynucleotides encoding the receptor can be obtained by other routes. Automated techniques of gene synthesis and/or amplification can be performed to generate DNA coding therefor. Because of the length of the human GluR1B receptor-encoding DNA, application of automated synthesis may require staged gene construction, in which regions of the gene up to about 300 nucleotides in length are synthesized individually and then ligated in correct succession by overhang complementarity for final assembly. Individually synthesized gene regions can be amplified prior to assembly, using established polymerase chain reaction (PCR) technology.

The application of automated gene synthesis techniques provides an opportunity for generating polynucleotides that encode variants of the naturally occurring human GluR1B receptor. It will be appreciated, for example, that polynucleotides coding for the receptor can be generated by substituting synonymous codons for those represented in the naturally occurring polynucleotide sequences herein identified. In addition, polynucleotides coding for human GluR1B receptor variants can be generated which for example incorporate one or more, e.g. 1 to 10, single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the *E. coil* gpt gene which confers resistance to mycophenolic acid, the neogene from transposon Tn5 which confers resistance to the antibiotic G418 and to neomycin, the dhfr sequence from murine cells or *E. coli* which changes the phenotype of DHFR− cells into DHFR+ cells, and the tk gene of herpes simplex virus, which makes TK− cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a substance, i.e., a candidate ligand, to human GluR1B receptor of the invention is evaluated typically using a predetermined amount of cell-derived membrane (measured for example by protein determination), generally from about 25 ug to 100 ug. Generally, competitive binding assays will be useful to evaluate the affinity of a test compound relative to AMPA. This competitive binding assay can be performed by incubating the membrane preparation with radiolabelled AMPA, for example [3H]-AMPA, in the presence of unlabelled test compound added at varying concentrations. Following incubation, either displaced or bound radiolabelled AMPA can be recovered and measured, to determine the relative binding affinities of the test compound and AMPA for the particular receptor used as substrate. In this way, the affinities of various compounds for the AMPA-binding human CNS receptors can be measured. Alternatively, a radiolabelled analogue of glutamate may be employed in place of radiolabelled AMPA, as competing ligand.

As an alternative to using cells that express receptor-encoding DNA, ligand characterization may also be performed using cells for example Xenopus oocytes, that yield functional membrane-bound receptor following introduction by injection either of receptor-encoding messenger RNA into the oocyte cytoplasm, or of receptor-encoding DNA into the oocyte nucleus. To generate the messenger RNA of cytoplasmic delivery, the receptor-encoding DNA is typically subcloned first into a plasmidic vector adjacent a suitable promoter region, such as the T3 or T7 bacteriophage promoters, to enable transcription into RNA message. RNA is then transcribed from the inserted gene in vitro, collected and then injected into Xenopus oocytes. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell, in the established manner.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the human GluR1B receptor responsible for AMPA-binding resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length human GluR receptor-encoding DNA may be modified by site-directed mutagenesis, so as to introduce a translational stop codon into the extracellular N-terminal region, immediately before the sequence encoding the first transmembrane domain (TM1), i.e., before residue 521 as shown in FIG. 1 and SEQ ID NOs. 1 and 2. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 809–888 inclusive (FIG. 1 and SEQ ID NOs. 1 and 2). In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such AMPA-binding fragments of the human GluR1B receptor may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. *Aspergillus nidulans*, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of a human GluR1B receptor, for example in brain tissue, the present invention also provides, in another of its aspects, labelled antibody to the human GluR1B receptor. To raise such antibodies, there may be used as immunogen either the intact, soluble receptor or an immunogenic fragment thereof i.e. a fragment capable of eliciting an immune response, produced in a microbial or mammalian cell host as described above or by standard peptide synthesis techniques. Regions of human GluR1B receptor particularly suitable for use as immunogenic fragments include those corresponding in sequence to an extracellular region of the receptor, or a portion of the extracellular region, such as peptides consisting of residues 1–520 or a fragment thereof comprising at least about 10 residues, including particularly fragments containing residues 171–186 or 473–516; and peptides corresponding to the region between transmembrane domains TM-2 and TM-3, such as a peptide consisting of residues 586–595. Peptides consisting of the C-terminal domain (residues 809–888), or fragment thereof, may also be used for the raising of antibodies.

The raising of antibodies to the selected human GluR1B receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for a human GluR1B receptor, and selected regions thereof, may also be used, in accordance with another aspect of the present invention, as hybridization probes for example to identify sequence-related genes resident in the human or other mammalian genomes (or cDNA libraries) or to locate the human GluR1 B-encoding DNA in a specimen, such as brain tissue. This can be done using either the intact coding region, or a fragment thereof having radiolabelled e.g. 32p, nucleotides incorporated therein. To identify the human GluR1 B-encoding DNA in a specimen, it is desirable to use either the full length cDNA coding therefor, or a fragment which is unique thereto. With reference to FIG. 1, such nucleotide fragments include those comprising at least about 17 nucleic acids, and otherwise corresponding in sequence to a region coding for the extracellular N-terminal or C-terminal region of the receptor, or representing a 5'-untranslated or 3'-untranslated region thereof. Such oligonucleotide sequences, and the intact gene itself, may also be used of course to clone human GluR1 B-related human genes, particularly cDNA equivalents thereof, by standard hybridization techniques.

EXAMPLE 1

Isolation of DNA coding for the human GluR1B receptor cDNA coding for the human GluR1B receptor was identified by probing human fetal brain cDNA that was obtained as an EcoRI-based lambda phage library (lambda ZAP) from Stratagene Cloning Systems (La Jolla, Calif., U.S.A.). The cDNA library was screened using an oligonucleotide probe capable of annealing to the 5' region of the rat GluR1 receptor sequence reported by Hollmann et al, supra. The specific sequence of the 32-P-labelled probe is provided below: (SEQ ID NOs:5) 5'-CCAGATCGATATTGTGAA-CATCAGCGACACGTTTGAGATG-3'

The fetal brain cDNA library was screened under the following hybridization conditions; 6×SSC, 25% formamide, 5% Dernhardt's solution, 0.5% SDS, 100 ug/ml denatured salmon sperm DNA, 42C. Filters were washed with 2×SSC containing 0.5% SDS at 25C for 5 minutes, followed by a 15 minute wash at 50C with 2×SSC containing 0.5% SDS. The final wash was with 1×SSC containing 0.5% SDS at 50C for 15 minutes. Filters were exposed to X-ray film (Kodak) overnight. Of 10⁶ clones screened, only one cDNA insert, of about 3.2 kb, was identified, and designated RKCSFG91, For sequencing, the '91 phage was plaque purified, then excised as a phagemid according to the supplier's specifications, to generate an insert-carrying Bluescript-SK variant of the phagemid vector. Sequencing of the '91 clone across its entire sequence revealed a putative ATG initiation codon together with about 61 bases of 5non-coding region and 2,718 bases of coding region. Also revealed was a termination codon, as well as about 438 bases of 3' non-translated sequence. The entire sequence of the EcoRI/EcoRI insert is provided in FIG. 1 and SEQ ID NO:1.

A 6.2 kb phagemid designated pBS/humGluR1B, carrying the receptor-encoding DNA as a 3.2 kb EcoRI/EcoRI insert in a 3.0 kb Bluescript-SK phagemid background, was deposited, under the terms of the Budapest Treaty, with the American Type Culture Collection in Rockville, Md. U.S.A. on May 28, 1992, and has been assigned accession number ATCC 75246.

EXAMPLE 2

Construction of genetically engineered cells producing human GluR1B receptor

For transient expression in mammalian cells, cDNA coding for the human GluR1B receptor was incorporated into the mammalian expression vector pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and antisense RNA transcripts and a Col E1-like high copy plasmid origin. A polylinker is located appropriately downstream of the CMV promoter (and 3' of the T7 promoter).

The strategy depicted in FIG. 2 was employed to facilitate incorporation of the GluR1B receptor-encoding cDNA into an expression vector. Particularly, a NotI site was introduced onto the 3' flank of the Bluescript-SK cDNA insert, and the cDNA insert was then released from pBS/humGluR1B as a 3.2 kb NotI/NotI fragment, which was then incorporated at the NotI site in the pcDNAI polylinker. Sequencing across the junctions was performed, to confirm proper insert orientation in pcDNA1. The resulting plasmid, designated pcDNA1/humGluR1B, was then introduced for transient expression into a selected mammalian cell host, in this case the monkey-derived, fibroblast like cells of the COS-1 lineage (available from the American Type Culture Collection, Rockville, Md. as ATCC CRL 1650).

For transient expression of the GluR1B-encoding DNA, COS-1 cells were transfected with approximately 8 ug DNA (as pcDNA1/humGluR2B) per 10⁶ COS cells, by DEAE-mediated DNA transfection and treated with chloroquine according to the procedures described by Maniatis et al, supra. Briefly, COS-1 cells were plated at a density of 5×10⁶ cells/dish and then grown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 uM chloroquine, 10% NuSerum, DNA (0.4 mg/ml)in DMEM/F12 medium.

After incubation for 3 hours at 37C, cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines can also prepared using two different cell types as host: CHO K1 and CHO Pro5. To construct these cell lines, cDNA coding for human GluR1B is incorporated into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of 5×10⁵ in 10% FBS-supplemented MEM medium. After growth for 24 hours, fresh medium are added to the plates and three hours later, the cells are transfected using the calcium phosphate-DNA co-precipitation procedure (Maniatis et al, supra). Briefly, 3 ug of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 3

Ligand binding assays

Transfected cells in the frozen state were resuspended in ice-cold distilled water using a hand homogenizer, sonicated for 5 seconds, and then centrifuged for 20 minutes at 50,000 g. The supernatant was discarded and the membrane pellet stored frozen at −70° C.

COS cell membrane pellets were suspended in ice cold 50 mM Tris-HCl (pH 7.55, 5C) and centrifuged again at 50,000 g for 10 minutes in order to remove endogenous glutamate that would compete for binding. Pellets were resuspended in ice cold 50 mM Tris-HCl (pH 7.55) buffer and the resultant membrane preparation was used as tissue source for binding experiments described below. Proteins were determined using the Pierce Reagent with BSA as standard.

Binding assays were then performed, using an amount of COS-derived membrane equivalent to from 25–100 ug as judged by protein determination and selected radiolabelled ligand. In particular, for AMPA-binding assays, incubation mixtures consisted of 25–100 ug tissue protein and D,L-alpha-[5-methyl-3H]amino-3-hydroxy-5-methylisoxazole-4-propionic acid (3H-AMPA, 27.6Ci/mmole, 10 nM final) with 0.1M KSCN and 2.5 mM $CaCl_2$ in the 1 ml final volume. Non-specific binding was determined in the presence of 1 mM L-glutamate. Samples were incubated on ice for 60 minutes in plastic minivials, and bound and free ligand were separated by centrifugation for 30 minutes at 50,000 g. Pellets were washed twice in 4 ml of the cold incubation buffer, then 5 ml of Beckman Ready-Protein Plus scintillation cocktail was added, for counting.

For kainate-binding assays, incubation mixtures consisted of 25–100 ug tissue protein and [vinylidene-3H] kainic acid (58Ci/mmole, 5 nM final) in the cold incubation buffer, 1 ml final volume. Non-specific binding was determined in the presence of 1 mM L-glutamate. Samples were incubated as for the AMPA-binding assays, and bound and free ligand were separated by rapid filtration using a Brandel cell harvester and GF/B filters pre-soaked in ice-cold 0.3% polyethyleneimine. Filters were washed twice in 6 ml of the cold incubation buffer, then placed in scintillation vials with 5 ml of Beckman Ready-Protein Plus scintillation cocktail for counting.

Assays performed in this manner, using membrane preparations derived from the human GluR1B receptor-producing COS cells, revealed specific binding of about 100–150 fmole/mg protein, at 10 nM [3H]-AMPA (FIG. 3). Mock transfected cells exhibited no specific binding of any of the ligands tested. These results demonstrate clearly that the human GluR1B receptor is binding AMPA with specificity. This activity, coupled with the fact that there is little or no demonstrable binding of either kainate or NMDA, clearly assigns the human GluR1B receptor to be of the AMPA type of EAA receptor. Furthermore, this binding profile indicates that the receptor is binding in an authentic manner, and can therefore reliably predict the ligand binding "signature" of its non-recombinant counterpart from the human brain. These features make the recombinant receptor especially useful for selecting and characterizing ligand compounds which bind to the receptor, and/or for selecting and characterizing compounds which may act by displacing other ligands from the receptor. The isolation of the GluR1B receptor genes in substantially pure form, capable of being expressed as a single, homogeneous receptor species, therefore frees the ligand binding assay from the lack of precision introduced when complex, heterogeneous receptor preparations from human and other mammalian brains are used to attempt such characterizations.

We claim:

1. An isolated polynucleotide which encodes a protein having the sequence of SEQ ID NO:2.

2. An isolated polynucleotide according to claim 1, which consists of DNA.

3. An isolated polynucleotide according to claim 1, which consists of RNA.

4. A recombinant DNA vector having incorporated therein a polynucleotide which encodes a protein having the sequence of SEQ ID NO:2.

5. A recombinant DNA vector according to claim 4, wherein the polynucleotide incorporated therein is linked operably with DNA enabling expression and secretion of said receptor in a cellular host.

6. A recombinant DNA vector according to claim 5, which is the plasmid pBS/humGluR1B (ATCC 75246).

7. A 3.2 kilobase, EcoRI/EcoRI fragment of the recombinant DNA construct defined in claim 6.

8. A cellular host having incorporated therein a heterologous polynucleotide which encodes a protein having the sequence of SEQ ID NO:2.

9. A cellular host according to claim 8, which is a mammalian cell.

10. A membrane preparation derived from a cellular host as defined in claim 9.

11. A cellular host according to claim 8, which is an oocyte.

12. A membrane preparation derived from a cellular host as defined in claim 8.

13. A process for obtaining a substantially homogeneous source of a human GluR1B receptor, which comprises the steps of culturing a cellular host having incorporated expressibly therein a polynucleotide that encodes a protein having the sequence of SEQ ID NO:2, and then recovering the cultured cells.

14. A process for obtaining a substantially homogeneous source of a human GluR1B receptor according to claim 13, comprising the subsequent step of obtaining a membrane preparation from the cultured cells.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 3220 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 62..2782

( i x ) FEATURE:
        ( A ) NAME/KEY: sig_peptide
        ( B ) LOCATION: 62..115

( i x ) FEATURE:
        ( A ) NAME/KEY: mat_peptide
        ( B ) LOCATION: 116..2782

( x i ) SEQUENCE DESCRIPTION: SEQ ID NO:1:

```
GAATTCCACA   CCAAATCTAT   GATTGGACCT   GGGCTTCTTT   TTCGCCAATG   CAAAAAGGAA                    60

T ATG CAG CAC ATT TTT GCC TTC TTC TGC ACC GGT TTC CTA GGC GCG                                 106
  Met Gln His Ile Phe Ala Phe Phe Cys Thr Gly Phe Leu Gly Ala
  -18         -15                     -10                  -5

GTA GTA GGT GCC AAT TTC CCC AAC AAT ATC CAG ATC GGG GGA TTA TTT                               154
Val Val Gly Ala Asn Phe Pro Asn Asn Ile Gln Ile Gly Gly Leu Phe
            1               5                       10

CCA AAC CAG CAG TCA CAG GAA CAT GCT GCT TTT AGA TTT GCT TTG TCG                               202
Pro Asn Gln Gln Ser Gln Glu His Ala Ala Phe Arg Phe Ala Leu Ser
        15              20                      25

CAA CTC ACA GAG CCC CCG AAG CTG CTC CCC CAG ATT GAT ATT GTG AAC                               250
Gln Leu Thr Glu Pro Pro Lys Leu Leu Pro Gln Ile Asp Ile Val Asn
30              35                      40                      45

ATC AGC GAC ACG TTT GAG ATG ACC TAT AGA TTC TGT TCC CAG TTC TCC                               298
Ile Ser Asp Thr Phe Glu Met Thr Tyr Arg Phe Cys Ser Gln Phe Ser
```

-continued

|  |  |  | 50 |  |  |  |  | 55 |  |  |  |  | 60 |  |  |  |
|---|---|---|---|---|---|---|---|---|---|---|---|---|---|---|---|---|
| AAA | GGA | GTC | TAT | GCC | ATC | TTT | GGG | TTT | TAT | GAA | CGT | AGG | ACT | GTC | AAC | 346 |
| Lys | Gly | Val | Tyr | Ala | Ile | Phe | Gly | Phe | Tyr | Glu | Arg | Arg | Thr | Val | Asn |  |
|  |  |  | 65 |  |  |  |  | 70 |  |  |  |  | 75 |  |  |  |
| ATG | CTG | ACC | TCC | TTT | TGT | GGG | GCC | CTC | CAC | GTC | TGC | TTC | ATT | ACG | CCG | 394 |
| Met | Leu | Thr | Ser | Phe | Cys | Gly | Ala | Leu | His | Val | Cys | Phe | Ile | Thr | Pro |  |
|  |  |  | 80 |  |  |  |  | 85 |  |  |  |  | 90 |  |  |  |
| AGC | TTT | CCC | GTT | GAT | ACA | TCC | AAT | CAG | TTT | GTC | CTT | CAG | CTG | CGC | CCT | 442 |
| Ser | Phe | Pro | Val | Asp | Thr | Ser | Asn | Gln | Phe | Val | Leu | Gln | Leu | Arg | Pro |  |
|  | 95 |  |  |  |  | 100 |  |  |  |  | 105 |  |  |  |  |  |
| GAA | CTG | CAG | GAT | GCC | CTC | ATC | AGC | ATC | ATT | GAC | CAT | TAC | AAG | TGG | CAG | 490 |
| Glu | Leu | Gln | Asp | Ala | Leu | Ile | Ser | Ile | Ile | Asp | His | Tyr | Lys | Trp | Gln |  |
| 110 |  |  |  |  | 115 |  |  |  |  | 120 |  |  |  |  | 125 |  |
| AAA | TTT | GTC | TAC | ATT | TAT | GAT | GCC | GAC | CGG | GGC | TTA | TCC | GTC | CTG | CAG | 538 |
| Lys | Phe | Val | Tyr | Ile | Tyr | Asp | Ala | Asp | Arg | Gly | Leu | Ser | Val | Leu | Gln |  |
|  |  |  |  | 130 |  |  |  |  | 135 |  |  |  |  | 140 |  |  |
| AAA | GTC | CTG | GAT | ACA | GCT | GCT | GAG | AAG | AAC | TGG | CAG | GTG | ACA | GCA | GTC | 586 |
| Lys | Val | Leu | Asp | Thr | Ala | Ala | Glu | Lys | Asn | Trp | Gln | Val | Thr | Ala | Val |  |
|  |  |  | 145 |  |  |  |  | 150 |  |  |  |  | 155 |  |  |  |
| AAC | ATT | TTG | ACA | ACC | ACA | GAG | GAG | GGA | TAC | CGG | ATG | CTC | TTT | CAG | GAC | 634 |
| Asn | Ile | Leu | Thr | Thr | Thr | Glu | Glu | Gly | Tyr | Arg | Met | Leu | Phe | Gln | Asp |  |
|  |  | 160 |  |  |  |  | 165 |  |  |  |  | 170 |  |  |  |  |
| CTG | GAG | AAG | AAA | AAG | GAG | CGG | CTG | GTG | GTG | GTG | GAC | TGT | GAA | TCA | GAA | 682 |
| Leu | Glu | Lys | Lys | Lys | Glu | Arg | Leu | Val | Val | Val | Asp | Cys | Glu | Ser | Glu |  |
| 175 |  |  |  |  | 180 |  |  |  |  | 185 |  |  |  |  |  |  |
| CGC | CTC | AAT | GCT | ATC | TTG | GGC | CAG | ATT | ATA | AAG | CTA | GAG | AAG | AAT | GGC | 730 |
| Arg | Leu | Asn | Ala | Ile | Leu | Gly | Gln | Ile | Ile | Lys | Leu | Glu | Lys | Asn | Gly |  |
| 190 |  |  |  |  | 195 |  |  |  |  | 200 |  |  |  |  | 205 |  |
| ATC | GGC | TAC | CAC | TAC | ATT | CTT | GCA | AAT | CTG | GGC | TTC | ATG | GAC | ATT | GAC | 778 |
| Ile | Gly | Tyr | His | Tyr | Ile | Leu | Ala | Asn | Leu | Gly | Phe | Met | Asp | Ile | Asp |  |
|  |  |  |  | 210 |  |  |  |  | 215 |  |  |  |  | 220 |  |  |
| TTA | AAC | AAA | TTC | AAG | GAG | AGT | GGC | GCC | AAT | GTG | ACA | GGT | TTC | CAG | CTG | 826 |
| Leu | Asn | Lys | Phe | Lys | Glu | Ser | Gly | Ala | Asn | Val | Thr | Gly | Phe | Gln | Leu |  |
|  |  |  | 225 |  |  |  |  | 230 |  |  |  |  | 235 |  |  |  |
| GTG | AAC | TAC | ACA | GAC | ACT | ATT | CCG | GCC | AAG | ATC | ATG | CAG | CAG | TGG | AAG | 874 |
| Val | Asn | Tyr | Thr | Asp | Thr | Ile | Pro | Ala | Lys | Ile | Met | Gln | Gln | Trp | Lys |  |
|  |  | 240 |  |  |  |  | 245 |  |  |  |  | 250 |  |  |  |  |
| AAT | AGT | GAT | GCT | CGA | GAC | CAC | ACA | CGG | GTG | GAC | TGG | AAG | AGA | CCC | AAG | 922 |
| Asn | Ser | Asp | Ala | Arg | Asp | His | Thr | Arg | Val | Asp | Trp | Lys | Arg | Pro | Lys |  |
| 255 |  |  |  |  | 260 |  |  |  |  | 265 |  |  |  |  |  |  |
| TAC | ACC | TCT | GCG | CTC | ACC | TAC | GAT | GGG | GTG | AAG | GTG | ATG | GCT | GAG | GCT | 970 |
| Tyr | Thr | Ser | Ala | Leu | Thr | Tyr | Asp | Gly | Val | Lys | Val | Met | Ala | Glu | Ala |  |
| 270 |  |  |  |  | 275 |  |  |  |  | 280 |  |  |  |  | 285 |  |
| TTC | CAG | AGC | CTG | CGG | AGG | CAG | AGA | ATT | GAT | ATA | TCT | CGC | CGG | GGG | AAT | 1018 |
| Phe | Gln | Ser | Leu | Arg | Arg | Gln | Arg | Ile | Asp | Ile | Ser | Arg | Arg | Gly | Asn |  |
|  |  |  |  | 290 |  |  |  |  | 295 |  |  |  |  | 300 |  |  |
| GCT | GGG | GAT | TGT | CTG | GCT | AAC | CCA | GCT | GTT | CCC | TGG | GGC | CAA | GGG | ATC | 1066 |
| Ala | Gly | Asp | Cys | Leu | Ala | Asn | Pro | Ala | Val | Pro | Trp | Gly | Gln | Gly | Ile |  |
|  |  |  | 305 |  |  |  |  | 310 |  |  |  |  | 315 |  |  |  |
| GAC | ATC | CAG | AGA | GCT | CTG | CAG | CAG | GTG | CGA | TTT | GAA | GGT | TTA | ACA | GGA | 1114 |
| Asp | Ile | Gln | Arg | Ala | Leu | Gln | Gln | Val | Arg | Phe | Glu | Gly | Leu | Thr | Gly |  |
|  |  | 320 |  |  |  |  | 325 |  |  |  |  | 330 |  |  |  |  |
| AAC | GTG | CAG | TTT | AAT | GAG | AAA | GGA | CGC | CGG | ACC | AAC | TAC | ACG | CTC | CAC | 1162 |
| Asn | Val | Gln | Phe | Asn | Glu | Lys | Gly | Arg | Arg | Thr | Asn | Tyr | Thr | Leu | His |  |
| 335 |  |  |  |  | 340 |  |  |  |  | 345 |  |  |  |  |  |  |
| GTG | ATT | GAA | ATG | AAA | CAT | GAC | GGC | ATC | CGA | AAG | ATT | GGT | TAC | TGG | AAT | 1210 |
| Val | Ile | Glu | Met | Lys | His | Asp | Gly | Ile | Arg | Lys | Ile | Gly | Tyr | Trp | Asn |  |
| 350 |  |  |  |  | 355 |  |  |  |  | 360 |  |  |  |  | 365 |  |
| GAA | GAT | GAT | AAG | TTT | GTC | CCT | GCA | GCC | ACC | GAT | GCC | CAA | GCT | GGG | GGC | 1258 |
| Glu | Asp | Asp | Lys | Phe | Val | Pro | Ala | Ala | Thr | Asp | Ala | Gln | Ala | Gly | Gly |  |

|  |  |  |  |  |  |  |  |  |  |  |  |  |  |  |  |  |
|---|---|---|---|---|---|---|---|---|---|---|---|---|---|---|---|---|
|  |  |  |  |  | 370 |  |  |  |  | 375 |  |  |  |  | 380 |  |
| GAT | AAT | TCA | AGT | GTT | CAG | AAC | AGA | ACA | TAC | ATC | GTC | ACA | ACA | ATC | CTA | 1306 |
| Asp | Asn | Ser | Ser<br>385 | Val | Gln | Asn | Arg<br>390 | Thr | Tyr | Ile | Val | Thr<br>395 | Thr | Ile | Leu |  |
| GAA | GAT | CCT | TAT | GTG | ATG | CTC | AAG | AAG | AAC | GCC | AAT | CAG | TTT | GAG | GGC | 1354 |
| Glu | Asp | Pro<br>400 | Tyr | Val | Met | Leu | Lys<br>405 | Lys | Asn | Ala | Asn | Gln<br>410 | Phe | Glu | Gly |  |
| AAT | GAC | CGT | TAC | GAG | GGC | TAC | TGT | GTA | GAG | CTG | GCG | GCA | GAG | ATT | GCC | 1402 |
| Asn | Asp | Arg<br>415 | Tyr | Glu | Gly | Tyr | Cys<br>420 | Val | Glu | Leu | Ala | Ala<br>425 | Glu | Ile | Ala |  |
| AAG | CAC | GTG | GGC | TAC | TCC | TAC | CGT | CTG | GAG | ATT | GTC | AGT | GAT | GGA | AAA | 1450 |
| Lys<br>430 | His | Val | Gly | Tyr | Ser<br>435 | Tyr | Arg | Leu | Glu | Ile<br>440 | Val | Ser | Asp | Gly | Lys<br>445 |  |
| TAC | GGA | GCC | CGA | GAC | CCT | GAC | ACG | AAG | GCC | TGG | AAT | GGC | ATG | GTG | GGA | 1498 |
| Tyr | Gly | Ala | Arg | Asp<br>450 | Pro | Asp | Thr | Lys | Ala<br>455 | Trp | Asn | Gly | Met | Val<br>460 | Gly |  |
| GAG | CTG | GTC | TAT | GGA | AGA | GCA | GAT | GTG | GCT | GTG | GCT | CCC | TTA | ACT | ATC | 1546 |
| Glu | Leu | Val | Tyr<br>465 | Gly | Arg | Ala | Asp | Val<br>470 | Ala | Val | Ala | Pro | Leu<br>475 | Thr | Ile |  |
| ACT | TTG | GTC | CGG | GAA | GAA | GTT | ATA | GAT | TTC | TCC | AAA | CCA | TTT | ATG | AGT | 1594 |
| Thr | Leu | Val<br>480 | Arg | Glu | Glu | Val | Ile<br>485 | Asp | Phe | Ser | Lys | Pro<br>490 | Phe | Met | Ser |  |
| TTG | GGG | ATC | TCC | ATC | ATG | ATT | AAA | AAA | CCA | CAG | AAA | TCC | AAG | CCG | GGT | 1642 |
| Leu | Gly | Ile<br>495 | Ser | Ile | Met | Ile | Lys<br>500 | Lys | Pro | Gln | Lys | Ser<br>505 | Lys | Pro | Gly |  |
| GTC | TTC | TCC | TTC | CTT | GAT | CCT | TTG | GCT | TAT | GAG | ATT | TGG | ATG | TGC | ATT | 1690 |
| Val<br>510 | Phe | Ser | Phe | Leu | Asp<br>515 | Pro | Leu | Ala | Tyr | Glu<br>520 | Ile | Trp | Met | Cys | Ile<br>525 |  |
| GTT | TTT | GCC | TAC | ATT | GGA | GTG | AGT | GTT | GTC | CTC | TTC | CTG | GTC | AGC | CGC | 1738 |
| Val | Phe | Ala | Tyr | Ile<br>530 | Gly | Val | Ser | Val | Val<br>535 | Leu | Phe | Leu | Val | Ser<br>540 | Arg |  |
| TTC | AGT | CCC | TAT | GAA | TGG | CAC | AGT | GAA | GAG | TTT | GAG | GAA | GGA | CGG | GAC | 1786 |
| Phe | Ser | Pro | Tyr<br>545 | Glu | Trp | His | Ser | Glu<br>550 | Glu | Phe | Glu | Glu | Gly<br>555 | Arg | Asp |  |
| CAG | ACA | ACC | AGT | GAC | CAG | TCC | AAT | GAG | TTT | GGG | ATA | TTC | AAC | AGT | TTG | 1834 |
| Gln | Thr | Thr<br>560 | Ser | Asp | Gln | Ser | Asn<br>565 | Glu | Phe | Gly | Ile | Phe<br>570 | Asn | Ser | Leu |  |
| TGG | TTC | TCC | CTG | GGA | GCC | TTC | ATG | CAG | CAA | GGA | TGT | GAC | ATT | TCT | CCC | 1882 |
| Trp | Phe<br>575 | Ser | Leu | Gly | Ala | Phe<br>580 | Met | Gln | Gln | Gly | Cys<br>585 | Asp | Ile | Ser | Pro |  |
| AGG | TCC | CTG | TCT | GGT | CGC | ATC | GTT | GGT | GGC | GTC | TGG | TGG | TTC | TTC | ACC | 1930 |
| Arg<br>590 | Ser | Leu | Ser | Gly | Arg<br>595 | Ile | Val | Gly | Gly | Val<br>600 | Trp | Trp | Phe | Phe | Thr<br>605 |  |
| TTA | ATC | ATC | ATC | TCC | TCA | TAT | ACA | GCC | AAT | CTG | GCC | GCC | TTC | CTG | ACC | 1978 |
| Leu | Ile | Ile | Ile | Ser<br>610 | Ser | Tyr | Thr | Ala | Asn<br>615 | Leu | Ala | Ala | Phe | Leu<br>620 | Thr |  |
| GTG | GAG | AGG | ATG | GTG | TCT | CCC | ATT | GAG | AGT | GCA | GAG | GAC | CTA | GCG | AAC | 2026 |
| Val | Glu | Arg | Met | Val<br>625 | Ser | Pro | Ile | Glu<br>630 | Ser | Ala | Glu | Asp | Leu<br>635 | Ala | Asn |  |
| GAG | ACA | GAA | ATT | GCC | TAC | GGG | ACG | CTG | GAA | GCA | GGA | TCT | ACT | AAG | GAG | 2074 |
| Glu | Thr | Glu | Ile<br>640 | Ala | Tyr | Gly | Thr | Leu<br>645 | Glu | Ala | Gly | Ser | Thr<br>650 | Lys | Glu |  |
| TTC | TTC | AGG | AGG | TCT | AAA | ATT | GCT | GTG | TTT | GAG | AAG | ATG | TGG | ACA | TAC | 2122 |
| Phe | Phe | Arg<br>655 | Arg | Ser | Lys | Ile | Ala<br>660 | Val | Phe | Glu | Lys | Met<br>665 | Trp | Thr | Tyr |  |
| ATG | AAG | TCA | GCA | GAG | CCA | TCA | GTT | TTT | GTG | CGG | ACC | ACA | GAG | GAG | GGG | 2170 |
| Met<br>670 | Lys | Ser | Ala | Glu | Pro<br>675 | Ser | Val | Phe | Val | Arg<br>680 | Thr | Thr | Glu | Glu | Gly<br>685 |  |
| ATG | ATT | CGA | GTG | AGG | AAA | TCC | AAA | GGC | AAA | TAT | GCC | TAC | CTC | CTG | GAG | 2218 |
| Met | Ile | Arg | Val | Arg | Lys | Ser | Lys | Gly | Lys | Tyr | Ala | Tyr | Leu | Leu | Glu |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 690 |     |     |     |     | 695 |     |     |     |     | 700 |     |     |      |
| TCC | ACC | ATG | AAT | GAG | TAC | ATT | GAG | CAG | CGG | AAA | CCC | TGT | GAC | ACC | ATG | 2266 |
| Ser | Thr | Met | Asn<br>705 | Glu | Tyr | Ile | Glu | Gln<br>710 | Arg | Lys | Pro | Cys | Asp<br>715 | Thr | Met |      |
| AAG | GTG | GGA | GGT | AAC | TTG | GAT | TCC | AAA | GGC | TAT | GGC | ATT | GCA | ACA | CCC | 2314 |
| Lys | Val | Gly<br>720 | Gly | Asn | Leu | Asp | Ser | Lys<br>725 | Gly | Tyr | Gly | Ile<br>730 | Ala | Thr | Pro |      |
| AAG | GGG | TCT | GCC | CTG | AGA | GGT | CCC | GTA | AAC | CTA | GCG | GTT | TTG | AAA | CTC | 2362 |
| Lys | Gly | Ser<br>735 | Ala | Leu | Arg | Gly<br>740 | Pro | Val | Asn | Leu | Ala<br>745 | Val | Leu | Lys | Leu |      |
| AGT | GAG | CAA | GGC | GTC | TTA | GAC | AAG | CTG | AAA | AGC | AAA | TGG | TGG | TAC | GAT | 2410 |
| Ser<br>750 | Glu | Gln | Gly | Val | Leu<br>755 | Asp | Lys | Leu | Lys | Ser<br>760 | Lys | Trp | Trp | Tyr | Asp<br>765 |      |
| AAA | GGG | GAA | TGT | GGA | AGC | AAG | GAC | TCC | GGA | AGT | AAG | GAC | AAG | ACA | AGC | 2458 |
| Lys | Gly | Glu | Cys | Gly<br>770 | Ser | Lys | Asp | Ser | Gly<br>775 | Ser | Lys | Asp | Lys | Thr<br>780 | Ser |      |
| GCT | CTG | AGC | CTC | AGC | AAT | GTG | GCA | GGC | GTG | TTC | TAC | ATC | CTG | ATC | GGA | 2506 |
| Ala | Leu | Ser | Leu<br>785 | Ser | Asn | Val | Ala | Gly<br>790 | Val | Phe | Tyr | Ile | Leu<br>795 | Ile | Gly |      |
| GGA | CTT | GGA | CTA | GCC | ATG | CTG | GTT | GCC | TTA | ATC | GAG | TTC | TGC | TAC | AAA | 2554 |
| Gly | Leu | Gly<br>800 | Leu | Ala | Met | Leu | Val<br>805 | Ala | Leu | Ile | Glu | Phe<br>810 | Cys | Tyr | Lys |      |
| TCC | CGT | AGT | GAA | TCC | AAG | CGG | ATG | AAG | GGT | TTT | TGT | TTG | ATC | CCA | CAG | 2602 |
| Ser | Arg | Ser<br>815 | Glu | Ser | Lys | Arg | Met<br>820 | Lys | Gly | Phe | Cys | Leu<br>825 | Ile | Pro | Gln |      |
| CAA | TCC | ATC | AAC | GAA | GCC | ATA | CGG | ACA | TCG | ACC | CTC | CCC | CGC | AAC | AGC | 2650 |
| Gln | Ser<br>830 | Ile | Asn | Glu | Ala | Ile<br>835 | Arg | Thr | Ser | Thr<br>840 | Leu | Pro | Arg | Asn | Ser<br>845 |      |
| GGG | GCA | GGA | GCC | AGC | AGC | GGC | GGC | AGT | GGA | GAG | AAT | GGT | CGG | GTG | GTC | 2698 |
| Gly | Ala | Gly | Ala | Ser<br>850 | Ser | Gly | Gly | Ser | Gly<br>855 | Glu | Asn | Gly | Arg | Val<br>860 | Val |      |
| AGC | CAT | GAC | TTC | CCC | AAG | TCC | ATG | CAA | TCG | ATT | CCT | TGC | ATG | AGC | CAC | 2746 |
| Ser | His | Asp | Phe<br>865 | Pro | Lys | Ser | Met | Gln<br>870 | Ser | Ile | Pro | Cys | Met<br>875 | Ser | His |      |
| AGT | TCA | GGG | ATG | CCC | TTG | GGA | GCC | ACG | GGA | TTG | TAA | CTGGAGC | AGATGGAGAC |  |  | 2799 |
| Ser | Ser | Gly<br>880 | Met | Pro | Leu | Gly | Ala<br>885 | Thr | Gly | Leu |     |     |     |     |     |      |

```
CCCTTGGGGA GCAGGCTCGG GCTCCCCAGC CCCATCCCAA ACCCTTCAGT GCCAAAAACA   2859
ACAACAAAAT AGAAAGCGCA ACCACCACCA ACCACTGCGA CCACAAGAAG GATGATTCAA   2919
CAGGTTTTCC TGAAGAATTG AAAAACCATT TTGCTGTCCC TTTTCCTTTT TTGATGTTCT   2979
TTCACCCTTT TCTGTTTGCT AAGTGAGGAT GAAAAATAA CACTGTACTG CAATAAGGGG    3039
AGAGTAACCC TGTCTAATGA AACCTGTGTC TCTGAGAGTA GAGTCACTGG AACACTAATG   3099
AGGAAACTGC ACTGTTTTAT TTAATTCAG TTGTTAGTGT GTCTTAGTGT GTGCAATTTT    3159
TTTTCTTACT AATATCCATG GTTTGCAGGT TCTGTTAGGC CCTTTCCTTC TCCTGGAATT   3219
C                                                                  3220
```

( 2 ) INFORMATION FOR SEQ ID NO:2:

( i ) SEQUENCE CHARACTERISTICS:
        ( A ) LENGTH: 906 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Gln | His | Ile | Phe | Ala | Phe | Phe | Cys | Thr | Gly | Phe | Leu | Gly | Ala | Val |
|-----|-----|-----|-----|-----|-----|-----|-----|-----|-----|-----|-----|-----|-----|-----|-----|
| -18 |     |     | -15 |     |     |     | -10 |     |     |     |     | -5  |     |     |     |

| Val | Gly | Ala | Asn | Phe | Pro | Asn | Asn | Ile | Gln | Ile | Gly | Gly | Leu | Phe | Pro |
|---|---|---|---|---|---|---|---|---|---|---|---|---|---|---|---|
| | | 1 | | | 5 | | | | | 10 | | | | | |

Asn Gln Gln Ser Gln Glu His Ala Ala Phe Arg Phe Ala Leu Ser Gln
15                    20                  25                    30

Leu Thr Glu Pro Pro Lys Leu Leu Pro Gln Ile Asp Ile Val Asn Ile
            35                  40                        45

Ser Asp Thr Phe Glu Met Thr Tyr Arg Phe Cys Ser Gln Phe Ser Lys
              50                55                60

Gly Val Tyr Ala Ile Phe Gly Phe Tyr Glu Arg Arg Thr Val Asn Met
          65              70                75

Leu Thr Ser Phe Cys Gly Ala Leu His Val Cys Phe Ile Thr Pro Ser
        80              85              90

Phe Pro Val Asp Thr Ser Asn Gln Phe Val Leu Gln Leu Arg Pro Glu
95                  100               105                   110

Leu Gln Asp Ala Leu Ile Ser Ile Ile Asp His Tyr Lys Trp Gln Lys
              115                120                125

Phe Val Tyr Ile Tyr Asp Ala Asp Arg Gly Leu Ser Val Leu Gln Lys
            130             135                 140

Val Leu Asp Thr Ala Ala Glu Lys Asn Trp Gln Val Thr Ala Val Asn
        145             150                 155

Ile Leu Thr Thr Thr Glu Glu Gly Tyr Arg Met Leu Phe Gln Asp Leu
    160             165                 170

Glu Lys Lys Lys Glu Arg Leu Val Val Val Asp Cys Glu Ser Glu Arg
175                 180                 185                   190

Leu Asn Ala Ile Leu Gly Gln Ile Ile Lys Leu Glu Lys Asn Gly Ile
              195                 200                   205

Gly Tyr His Tyr Ile Leu Ala Asn Leu Gly Phe Met Asp Ile Asp Leu
            210                 215                 220

Asn Lys Phe Lys Glu Ser Gly Ala Asn Val Thr Gly Phe Gln Leu Val
        225                 230                 235

Asn Tyr Thr Asp Thr Ile Pro Ala Lys Ile Met Gln Gln Trp Lys Asn
    240                 245                 250

Ser Asp Ala Arg Asp His Thr Arg Val Asp Trp Lys Arg Pro Lys Tyr
255                 260                 265                   270

Thr Ser Ala Leu Thr Tyr Asp Gly Val Lys Val Met Ala Glu Ala Phe
            275                 280                 285

Gln Ser Leu Arg Arg Gln Arg Ile Asp Ile Ser Arg Arg Gly Asn Ala
            290                 295                 300

Gly Asp Cys Leu Ala Asn Pro Ala Val Pro Trp Gly Gln Gly Ile Asp
        305                 310                 315

Ile Gln Arg Ala Leu Gln Gln Val Arg Phe Glu Gly Leu Thr Gly Asn
    320                 325                 330

Val Gln Phe Asn Glu Lys Gly Arg Arg Thr Asn Tyr Thr Leu His Val
335                 340                 345                   350

Ile Glu Met Lys His Asp Gly Ile Arg Lys Ile Gly Tyr Trp Asn Glu
                355                 360                 365

Asp Asp Lys Phe Val Pro Ala Ala Thr Asp Ala Gln Ala Gly Gly Asp
            370                 375                 380

Asn Ser Ser Val Gln Asn Arg Thr Tyr Ile Val Thr Thr Ile Leu Glu
        385                 390                 395

Asp Pro Tyr Val Met Leu Lys Lys Asn Ala Asn Gln Phe Glu Gly Asn
    400                 405                 410

Asp Arg Tyr Glu Gly Tyr Cys Val Glu Leu Ala Ala Glu Ile Ala Lys 415                              420                              425                              430

His    Val    Gly    Tyr    Ser    Tyr    Arg    Leu    Glu    Ile    Val    Ser    Asp    Gly    Lys    Tyr
                            435                          440                          445

Gly    Ala    Arg    Asp    Pro    Asp    Thr    Lys    Ala    Trp    Asn    Gly    Met    Val    Gly    Glu
                     450                          455                          460

Leu    Val    Tyr    Gly    Arg    Ala    Asp    Val    Ala    Val    Ala    Pro    Leu    Thr    Ile    Thr
              465                          470                          475

Leu    Val    Arg    Glu    Glu    Val    Ile    Asp    Phe    Ser    Lys    Pro    Phe    Met    Ser    Leu
       480                          485                          490

Gly    Ile    Ser    Ile    Met    Ile    Lys    Lys    Pro    Gln    Lys    Ser    Lys    Pro    Gly    Val
495                          500                          505                          510

Phe    Ser    Phe    Leu    Asp    Pro    Leu    Ala    Tyr    Glu    Ile    Trp    Met    Cys    Ile    Val
                            515                          520                          525

Phe    Ala    Tyr    Ile    Gly    Val    Ser    Val    Val    Leu    Phe    Leu    Val    Ser    Arg    Phe
                     530                          535                          540

Ser    Pro    Tyr    Glu    Trp    His    Ser    Glu    Glu    Phe    Glu    Glu    Gly    Arg    Asp    Gln
              545                          550                          555

Thr    Thr    Ser    Asp    Gln    Ser    Asn    Glu    Phe    Gly    Ile    Phe    Asn    Ser    Leu    Trp
       560                          565                          570

Phe    Ser    Leu    Gly    Ala    Phe    Met    Gln    Gln    Gly    Cys    Asp    Ile    Ser    Pro    Arg
575                          580                          585                          590

Ser    Leu    Ser    Gly    Arg    Ile    Val    Gly    Gly    Val    Trp    Trp    Phe    Phe    Thr    Leu
                     595                          600                          605

Ile    Ile    Ile    Ser    Ser    Tyr    Thr    Ala    Asn    Leu    Ala    Ala    Phe    Leu    Thr    Val
              610                          615                          620

Glu    Arg    Met    Val    Ser    Pro    Ile    Glu    Ser    Ala    Glu    Asp    Leu    Ala    Asn    Glu
       625                          630                          635

Thr    Glu    Ile    Ala    Tyr    Gly    Thr    Leu    Glu    Ala    Gly    Ser    Thr    Lys    Glu    Phe
640                          645                          650

Phe    Arg    Arg    Ser    Lys    Ile    Ala    Val    Phe    Glu    Lys    Met    Trp    Thr    Tyr    Met
655                          660                          665                          670

Lys    Ser    Ala    Glu    Pro    Ser    Val    Phe    Val    Arg    Thr    Thr    Glu    Glu    Gly    Met
                     675                          680                          685

Ile    Arg    Val    Arg    Lys    Ser    Lys    Gly    Lys    Tyr    Ala    Tyr    Leu    Leu    Glu    Ser
              690                          695                          700

Thr    Met    Asn    Glu    Tyr    Ile    Glu    Gln    Arg    Lys    Pro    Cys    Asp    Thr    Met    Lys
       705                          710                          715

Val    Gly    Gly    Asn    Leu    Asp    Ser    Lys    Gly    Tyr    Gly    Ile    Ala    Thr    Pro    Lys
       720                          725                          730

Gly    Ser    Ala    Leu    Arg    Gly    Pro    Val    Asn    Leu    Ala    Val    Leu    Lys    Leu    Ser
735                          740                          745                          750

Glu    Gln    Gly    Val    Leu    Asp    Lys    Leu    Lys    Ser    Lys    Trp    Trp    Tyr    Asp    Lys
                     755                          760                          765

Gly    Glu    Cys    Gly    Ser    Lys    Asp    Ser    Gly    Ser    Lys    Asp    Lys    Thr    Ser    Ala
                     770                          775                          780

Leu    Ser    Leu    Ser    Asn    Val    Ala    Gly    Val    Phe    Tyr    Ile    Leu    Ile    Gly    Gly
              785                          790                          795

Leu    Gly    Leu    Ala    Met    Leu    Val    Ala    Leu    Ile    Glu    Phe    Cys    Tyr    Lys    Ser
       800                          805                          810

Arg    Ser    Glu    Ser    Lys    Arg    Met    Lys    Gly    Phe    Cys    Leu    Ile    Pro    Gln    Gln
815                          820                          825                          830

Ser    Ile    Asn    Glu    Ala    Ile    Arg    Thr    Ser    Thr    Leu    Pro    Arg    Asn    Ser    Gly
                     835                          840                          845

```
Ala  Gly  Ala  Ser  Ser  Gly  Gly  Ser  Gly  Glu  Asn  Gly  Arg  Val  Val  Ser
               850                           855                      860

His  Asp  Phe  Pro  Lys  Ser  Met  Gln  Ser  Ile  Pro  Cys  Met  Ser  His  Ser
               865                      870                     875

Ser  Gly  Met  Pro  Leu  Gly  Ala  Thr  Gly  Leu
          880                      885
```

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:3:

```
AGCTTGCGGC CGC                                                              13
```

( 2 ) INFORMATION FOR SEQ ID NO:4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:4:

```
GCGGCCGCA                                                                    9
```

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:5:

```
CCAGATCGAT ATTGTGAACA TCAGCGACAC GTTTGAGATG                                 40
```